US012575922B2

(12) United States Patent
Park

(10) Patent No.: US 12,575,922 B2
(45) Date of Patent: Mar. 17, 2026

(54) ANTI-REFLUX VALVE FOR PREVENTING GASTROESOPHAGEAL REFLUX DISEASE

(71) Applicant: KOREA UNIVERSITY RESEARCH AND BUSINESS FOUNDATION, Seoul (KR)

(72) Inventor: Sung Soo Park, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 1200 days.

(21) Appl. No.: 17/601,081

(22) PCT Filed: Apr. 2, 2020

(86) PCT No.: PCT/KR2020/004490
§ 371 (c)(1),
(2) Date: Feb. 15, 2022

(87) PCT Pub. No.: WO2020/204616
PCT Pub. Date: Oct. 8, 2020

(65) Prior Publication Data
US 2022/0323195 A1      Oct. 13, 2022

(30) Foreign Application Priority Data

Apr. 4, 2019      (KR) ......................... 10-2019-0039792
Mar. 31, 2020      (KR) ......................... 10-2020-0038860

(51) Int. Cl.
*A61F 2/04*      (2013.01)
(52) U.S. Cl.
CPC .......... *A61F 2/04* (2013.01); *A61F 2002/044* (2013.01); *A61F 2230/0065* (2013.01); *A61F 2250/0013* (2013.01)

(58) Field of Classification Search
CPC .................. A61F 2/04; A61F 2002/044; A61F 2230/0065; A61B 2017/00827; A61B 2014/00827
USPC ....................................................... 623/23.68
See application file for complete search history.

(56) References Cited

U.S. PATENT DOCUMENTS

| | | | | |
|---|---|---|---|---|
| 4,657,019 A | * | 4/1987 | Walsh ..................... | A61B 17/30 606/210 |
| 4,820,304 A | * | 4/1989 | Depel ..................... | A61F 2/203 623/9 |
| 6,264,700 B1 | * | 7/2001 | Kilcoyne .................. | A61F 2/04 623/23.68 |

(Continued)

FOREIGN PATENT DOCUMENTS

WO      91-01117 A1      2/1991

OTHER PUBLICATIONS

International Search Report for PCT/KR2020/004490 mailed Jul. 23, 2020 from Korean Intellectual Property Office.

*Primary Examiner* — Jerrah Edwards
(74) *Attorney, Agent, or Firm* — Revolution IP, PLLC

(57) ABSTRACT

The present invention relates to an anti-reflux valve for preventing gastro-esophageal reflux disease and includes a body formed in a ring shape and fixed to an upper end of a gastro-esophagus; a reflux blocking plate coupled to an inner circumferential surface of the body to be rotatable in one direction; and a fixing clip coupled to an outer circumferential surface of the body to fix the body to the upper end of the gastro-esophagus.

5 Claims, 7 Drawing Sheets

(56)                    References Cited

U.S. PATENT DOCUMENTS

| | | | |
|---|---|---|---|
| 7,753,870 B2* | 7/2010 | Demarais | A61B 17/12099 |
| | | | 604/8 |
| 2005/0228504 A1 | 10/2005 | Demarais | |
| 2008/0208356 A1* | 8/2008 | Stack | A61F 5/0036 |
| | | | 623/23.65 |
| 2014/0275747 A1 | 9/2014 | Connor | |

* cited by examiner

10

(a)

(b)

(c)

(a)

(b)

(c)

(a)

(b)

40

130

T

ANTI-REFLUX VALVE FOR PREVENTING GASTROESOPHAGEAL REFLUX DISEASE

TECHNICAL FIELD

The present invention relates to an anti-reflux valve for preventing gastro-esophageal reflux disease, and more particularly, to an anti-reflux valve for preventing gastro-esophageal reflux disease which may be inserted into or mounted in an upper portion of a stomach of a patient with gastro-esophageal reflux disease to predict a potential effect of an anti-reflux surgery.

BACKGROUND

Gastro-esophageal reflux disease (GERD), which has been recognized as a common disease in the western society, is increasing in prevalence in Korea according to westernization of lifestyle and eating habits. As a result of domestic big data survey (healthcare research and development project HC17C0050 of Ministry of Health and Welfare), a prevalence rate was increased from 11.8% in 2012 to 19.1% in 2016, which shows a strong upward trend of 8% over 5 years.

Although drug therapy is the primary treatment for gastro-esophageal reflux disease, the number of patients who cannot stop taking the drug and take the standard dose for 12 consecutive weeks is estimated to be 110,000 in 2016, and the number of patients who receive more than double the standard dose due to inadequate symptom control with standard dose drug treatment is also estimated to be 7,000 in 2016 (result of HC17C0050 which is healthcare research and development project of Ministry of Health and Welfare).

Meanwhile, according to a research result of "Effect Comparison and Economic Evaluation of Surgical and Non-Surgical Treatment" which is a healthcare research and development project of the Ministry of Health and Welfare, in a prospective clinical study conducted for patients with intractable gastro-esophageal reflux disease, surgical treatment showed statistically superior results in symptom control, treatment satisfaction, and quality of life. In addition, in a surgical group, medical costs and frequency of medical use were reduced, and in conclusion, surgical treatment was confirmed as a treatment alternative with an absolute advantage in terms of cost-effectiveness.

In addition, according to a survey of "Korean Gastro-esophageal Reflux Disease Surgery Research Group" under the Korean Gastric Cancer Society, about 100 anti-reflux surgeries are being performed annually. Considering the above prevalence and the number of patients taking long-term treatment, it may be confirmed that the anti-reflux surgery is being performed in less than 0.5%. Although the advantages of surgery are excellent in terms of effectiveness and cost, only a small portion of the surgical subjects are being operated on because of the inconvenience of tests that have to be performed before surgery and non-guaranteed surgical effect due to lack of gold-standard test.

Accordingly, there is a demand for development of a medical device which may replace inconvenient tests and experience the effects of surgery by developing a diagnostic test method that may predict the effects of surgery in advance.

SUMMARY OF INVENTION

Technical Problem

An object of the present invention is to provide an anti-reflux valve for preventing gastro-esophageal reflux disease, which is inserted into or mounted in an upper portion of a stomach of a patient with gastro-esophageal reflux disease and may predict a potential effect of an anti-reflux surgery.

An object of the present invention is not limited to the above-described object, and the present invention may be applied to undescribed semiconductor facilities, pharmaceutical facilities, and so on and may be clearly understood by those skilled in the art to which the present invention belongs from the following description.

Solution to Problem

In order to achieve the object, an anti-reflux valve for preventing gastro-esophageal reflux disease which is installed in an upper portion of a stomach of a patient with gastro-esophageal reflux disease, according to an embodiment of the present invention, includes a body formed in a ring shape and fixed to an upper end of a gastro-esophagus; a reflux blocking plate coupled to an inner circumferential surface of the body to be rotatable in one direction; and a fixing clip coupled to an outer circumferential surface of the body to fix the body to the upper end of the gastro-esophagus.

Here, the fixing clip may be formed in a ring shape having one open region and coupled to the body to be fixed to the gastro-esophagus.

Here, the body may have at least one coupling hole to which the fixing clip is fixed, and the fixing clip may be coupled to the coupling hole to be coupled to the gastro-esophagus.

Here, the fixing clip may be formed of a biodegradable material.

Here, the body may have a fixing groove formed therein to correspond to a shape of the fixing clip.

Here, the reflux blocking plate may include a first reflux blocking plate and a second reflux blocking plate that are vertically stacked on the body and coupled to sequentially rotate.

An anti-reflux valve for preventing gastro-esophageal reflux disease which is installed in an upper portion of a stomach of a patient with gastro-esophageal reflux disease, according to an embodiment of the present invention, includes a body formed in a ring shape and fixed to an upper end of a gastro-esophagus; and a fixing clip coupled to the body to fix the body to the upper end of the gastro-esophagus, wherein the body may include a reflux blocking portion that is formed in a hopper shape having a diameter that is gradually reduced in a downward direction to prevent reflux.

Here, the reflux blocking portion may be wrinkled along a circumferential surface formed in the hopper shape.

Advantageous Effects

According to the present invention, an anti-reflux valve for preventing gastro-esophageal reflux disease may be inserted into or mounted in an upper portion of a stomach of a patient with gastro-esophageal reflux disease to prevent endocrine fluid secreted from the stomach or so on from refluxing through an upper end of the stomach, and thus, a potential effect of an anti-reflux surgery may be predicted.

Effects of the present invention is not limited to the above-described effects and may be applied to undescribed semiconductor facilities, pharmaceutical facilities, and so on, and other effects will be clearly understood by those skilled in the art to which the present invention belongs from the following description.

BEST MODE FOR INVENTION

Figure 1:
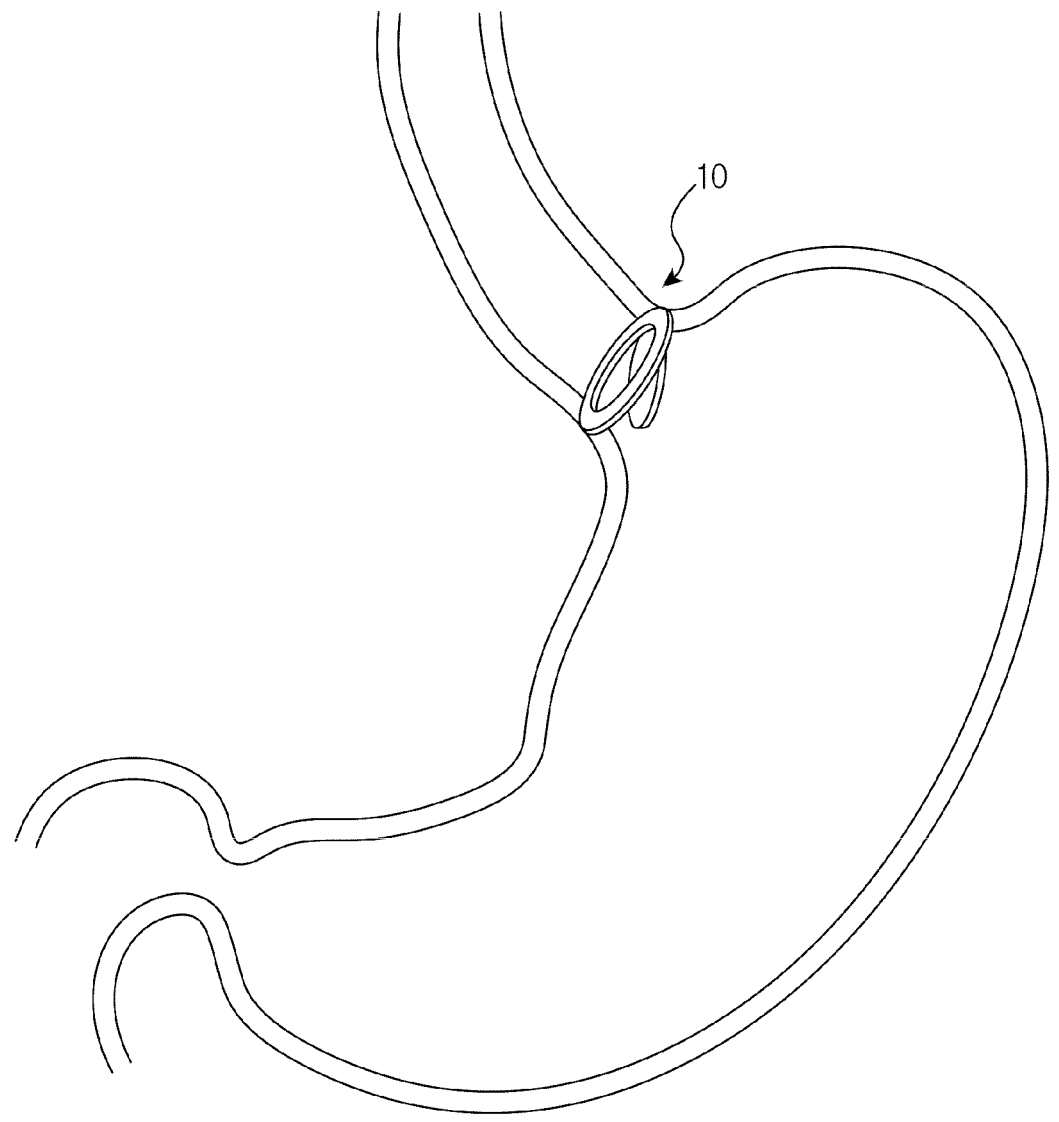
FIG. 1 is a conceptual view in which an anti-reflux valve for preventing gastro-esophageal reflux disease is mounted, according to an embodiment of the present invention.

Hereinafter, preferred embodiments of the present invention will be described in detail with reference to the accompanying drawings. In this case, in the accompanying drawings, the same components are denoted by the same reference numerals as much as possible. Detailed descriptions on well-known functions and configurations that may obscure the gist of the present invention are omitted. For the same reason, some components are exaggerated, omitted, or schematically illustrated in the accompanying drawings.

Throughout the specification, when a portion "includes" a certain component, this means that other components may be further included, rather than excluding the other components, unless otherwise stated. In addition, throughout the specification, "on" means to be located above or below a target portion and does not necessarily mean to be located above the target portion in a direction of gravity.

Figure 2:
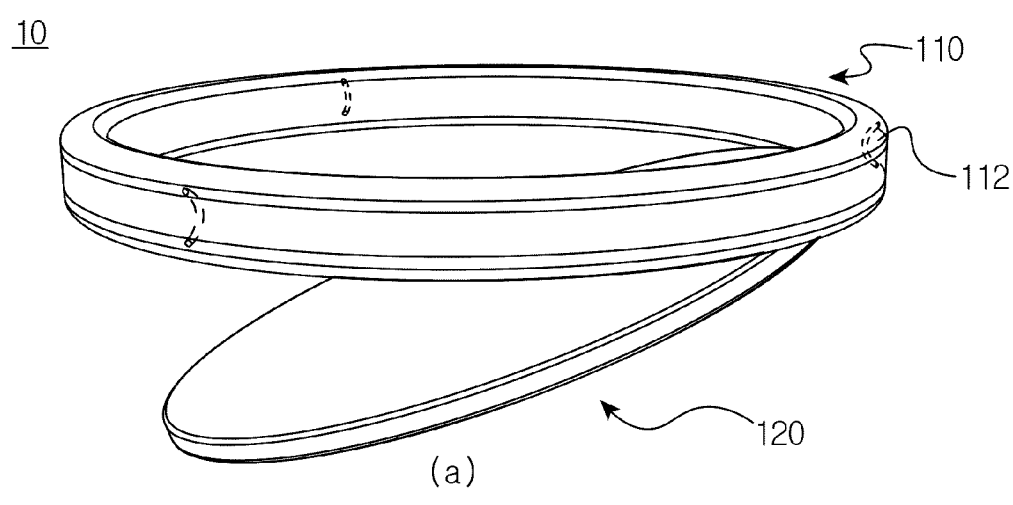
FIG. 2 illustrates views of an anti-reflux valve for preventing gastro-esophageal reflux disease, according to a first embodiment of the present invention.
Figure 2:
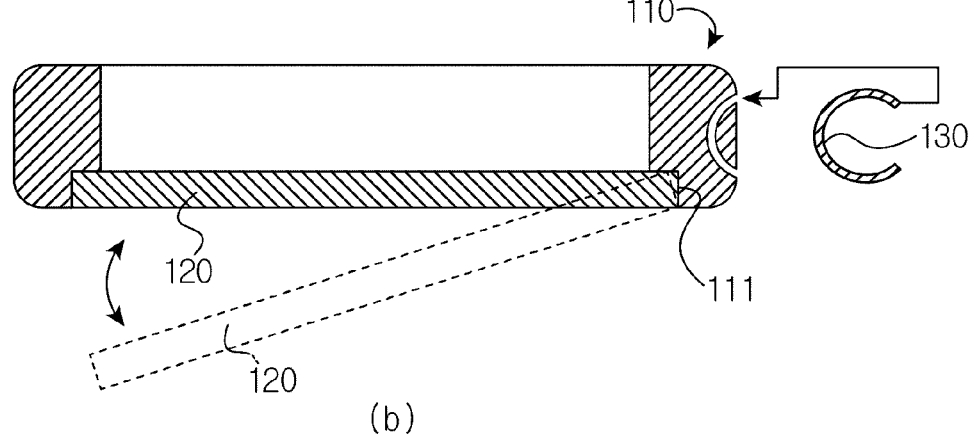
Figure 2:
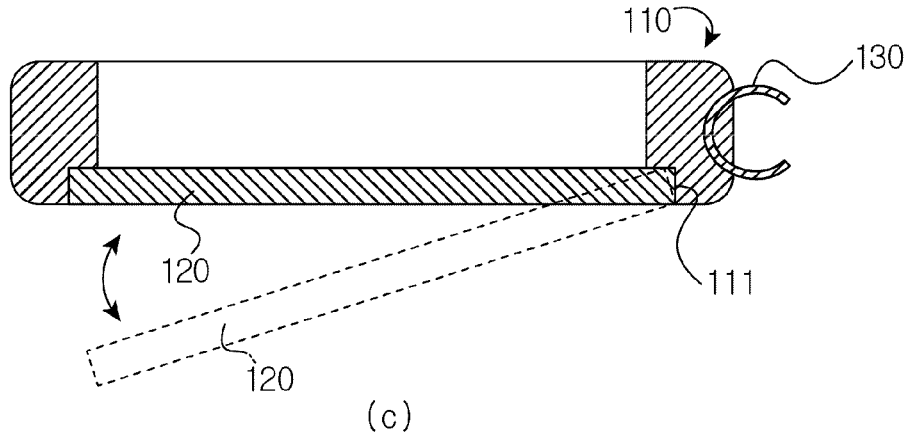

FIG. 1 is a conceptual view in which an anti-reflux valve 10 for preventing gastro-esophageal reflux disease is mounted according to an embodiment of the present invention, and FIG. 2 illustrates views of an anti-reflux valve 10 for preventing gastro-esophageal reflux disease, according to a first embodiment of the present invention.

A body 110 may be formed in a ring shape to be fixed to an upper end of a gastro-esophagus. A step difference portion 111 may be formed at a lower end of the body 110 such that a reflux blocking plate 120 is coupled to be rotatable in only one direction. In addition, a surface in contact with the reflux blocking plate 120 due the step difference portion 111 may be coated with a silicone material to increase adhesion with the reflux blocking plate 120.

In addition, the body 110 may have at least one coupling hole 112 to which the fixing clip 130 is fixed. Three coupling holes 112 may be formed along a circumferential direction of the body 110 at intervals of 120 degrees. The coupling hole 112 is formed in an arc shape from an upper outer side of the body 110 to an inner side.

In addition, the fixing clip 130 is formed in a ring shape having one open region. Therefore, because being formed in a ring shape, the fixing clip 130 is formed in an arc shape from the upper outer side to the inner side, a central region of the fixing clip 130 may be supported by the coupling hole 112, and both ends thereof may protrude out of the body 110 to be fixed in position through a clip fastening tool T illustrated in FIG. 7 thereon.

The reflux blocking plate 120 is coupled to the step difference portion 111 formed on an inner circumferential surface of the body 110 so as to be rotatable only in a downward direction. Therefore, the reflux blocking plate 120 is automatically rotated by a weight of food only when food or so on is ingested, and an open state is maintained. However, the reflux blocking plate 120 may provide stable food movement due to the step difference portion 111 in normal times and may not be rotated in an opposite direction, and thus, an endocrine fluid secreted by the stomach and so on may not flow backward through an upper part of the stomach.

Figure 3:
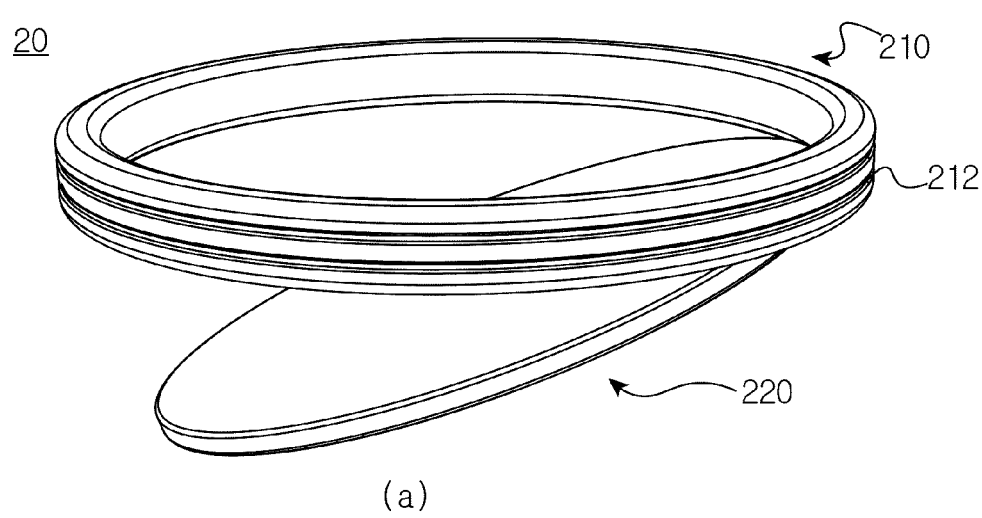
FIG. 3 illustrates views of an anti-reflux valve for preventing gastro-esophageal reflux disease, according to a second embodiment of the present invention.
Figure 3:
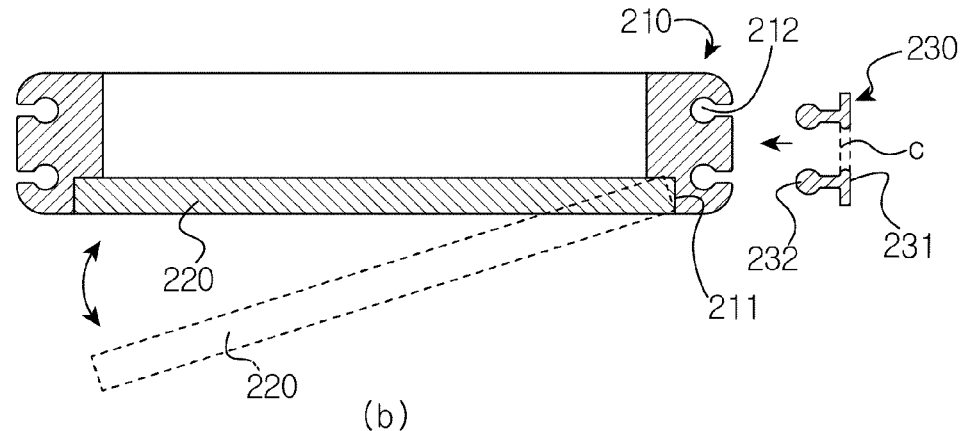
Figure 3:
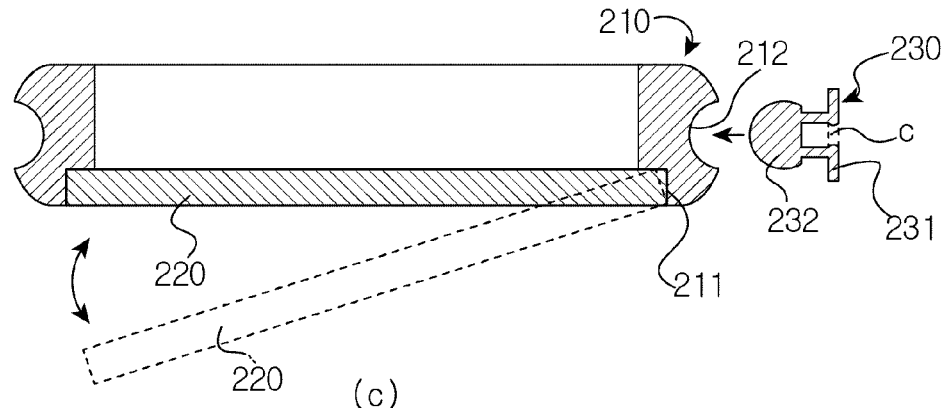

Referring to FIGS. 2 and 3, an anti-reflux valve 20 for preventing gastro-esophageal reflux disease, according to a second embodiment of the present invention is installed in an upper portion of the stomach to prevent gastro-esophageal reflux disease and may be formed with a body 210, a reflux blocking plate 220, and a fixing clip 230.

The reflux blocking plate 220 is coupled to the step difference portion 211 formed on an inner circumferential surface of the body 210 so as to be rotatable only in a downward direction. The body 210 is formed in a ring shape and fixed to an upper end of the gastro-esophagus. In addition, the body 210 has grooves 212 formed in a circumferential direction thereof. The grooves 212 are each formed such that an end in an insertion direction is relatively large compared to an entry direction, and thus, the fixing clip 230 to be described below may be prevented from being separated therefrom in an inserted state. Preferably, the grooves 212 are stacked in a vertical direction to stably fix the fixing clip 230.

The grooves 212 may be formed in an inwardly concave groove shape as another method. In addition, a certain region having a concave groove shape may be formed by magnetic force c. As such, when the certain region having the concave groove shape is formed by magnetic force c, in order to enable the fixing clip 230 to be described below to be coupled to the groove 212, a region corresponding thereto may be formed of a magnet.

The reflux blocking plate 220 is substantially the same as described above, detailed descriptions thereof are omitted below.

The fixing clip 230 may be coupled to the groove 212 formed on an outer circumferential surface of the body 210 to serve to fix the body 210 to an upper end of the gastro-esophagus, and a region fixed to the gastro-esophagus may be formed in a ring shape 231. In addition, a fixing portion 232 may be formed such that the other end of the ring shape 231 may be fixed to the groove 212. The fixing portion 232 is formed in a spherical shape in which a diameter of the fixing portion 232 is increased toward the front such that, when coupled to the groove 212, the fixing portion 232 is not easily separated therefrom. In this case, the fixing clip 230 may be formed of a biodegradable material, and there is no need for a separate process of separating the fixing clip 230 after separating the body 210, and thus, post-care after surgery and treatment may be simplified. In addition, as described above, the fixing clip 230 includes the fixing portion 232 that may be formed of a magnet material to be connected to the groove 212.

Figure 4:
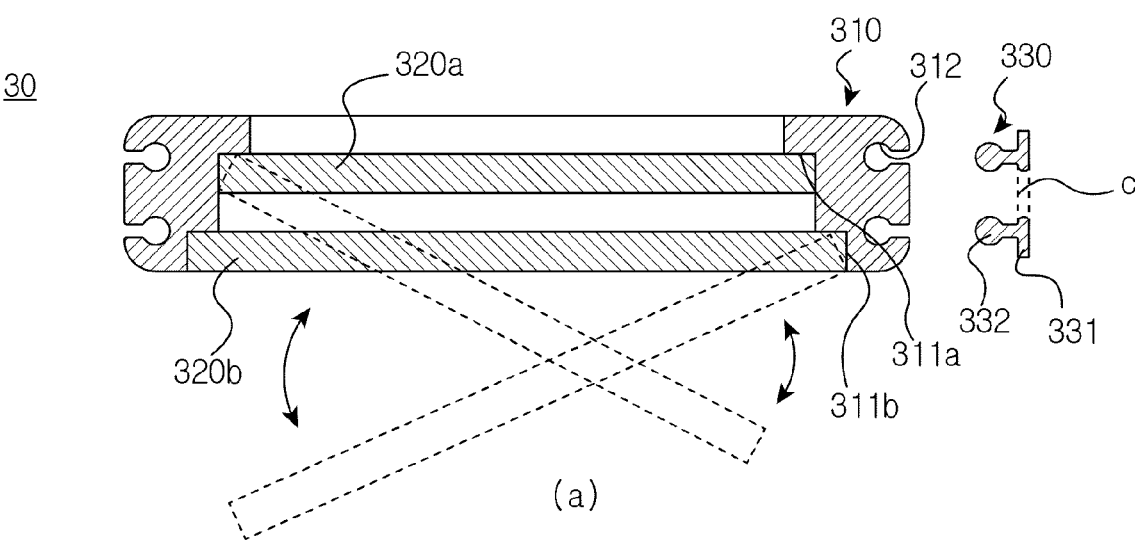
FIG. 4 illustrates views of an anti-reflux valve for preventing gastro-esophageal reflux disease, according to a third embodiment of the present invention.
Figure 4:
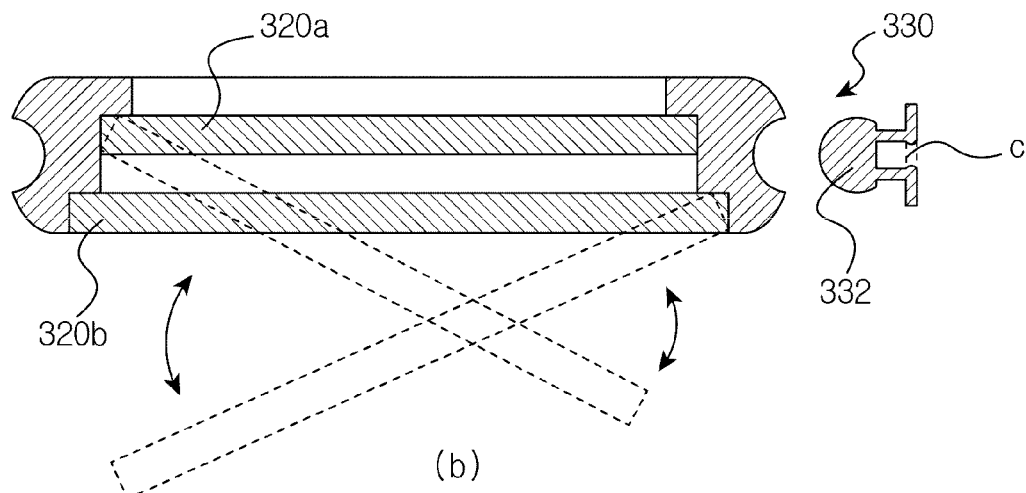

FIG. 4 illustrates views of an anti-reflux valve for preventing gastro-esophageal reflux disease according to a third embodiment of the present invention.

Referring to FIG. 4, an anti-reflux valve 30 for preventing gastro-esophageal reflux disease according to the third embodiment of the present invention may be formed with a body 310, a reflux blocking plate 320, and a fixing clip 330. Hereinafter, a coupling structure between the body 310 and the fixing clip 330 is the same as described above, such as, a fixing portion 332 may be formed such that the other end of the ring shape 331 may be fixed to the groove 312, and thus, detailed descriptions thereof are omitted below, and only structures of the body 310 and the reflux blocking plate 320 will be described in detail.

The body 310 has a first step difference portion 311a and a second step difference portion 311b formed in two stages in a downward direction, and the second step difference portion 311b is relatively larger than the first step difference portion 311a.

In addition, the reflux blocking plate 320 includes a first reflux blocking plate 320a and a second reflux blocking plate 320b, both plates are sequentially coupled to the first step difference portion 311a and the second step difference portion 311b. Therefore, food may be stably moved through sequential rotation of the first reflux blocking plate 320a and the second reflux blocking plate 320b according to the first step difference portion 311a and the second step difference portion 311b, and the first reflux blocking plate 320a and the second reflux blocking plate 320b may not be rotated in reverse, and thus, endocrine fluid secreted from the stomach and so on may not flow backward through an upper end of the stomach.

Figure 5:
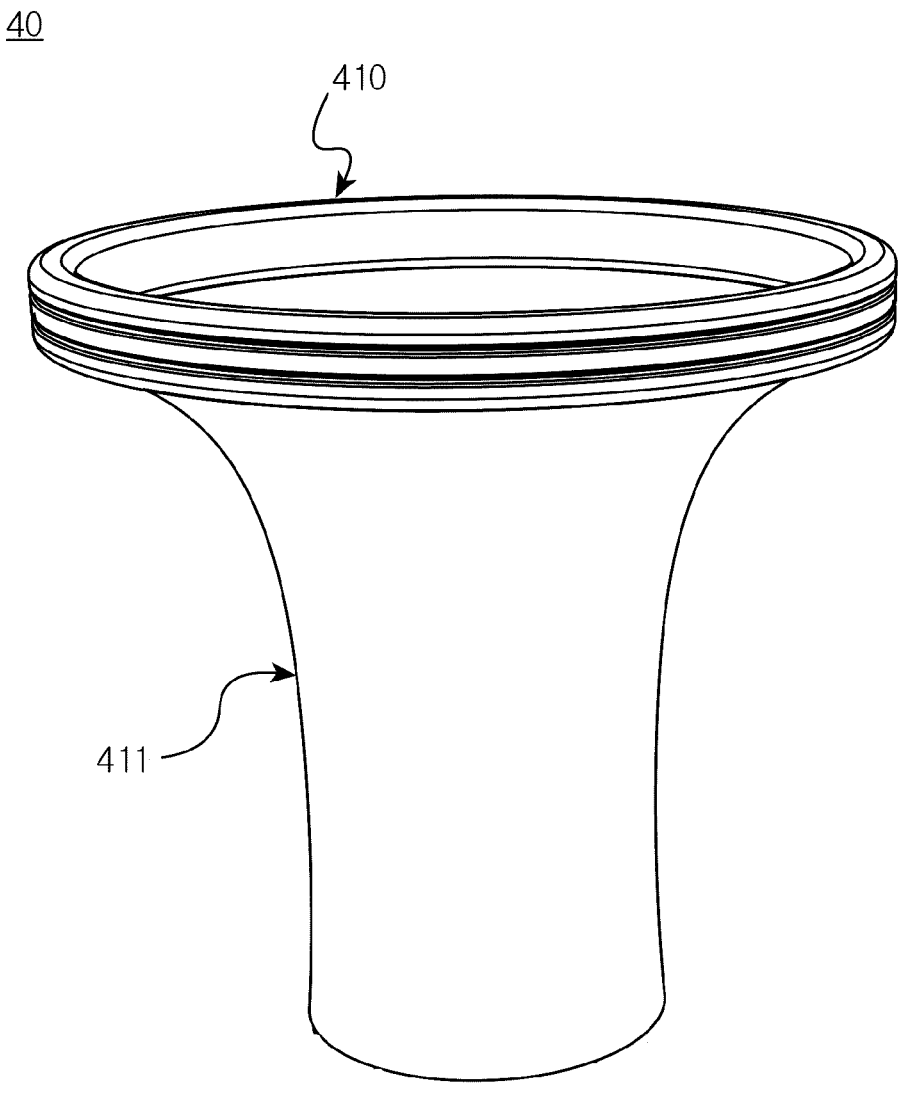
FIGS. 5 to 6 are views of an anti-reflux valve for preventing gastro-esophageal reflux disease, according to a fourth embodiment of the present invention.
Figure 6:
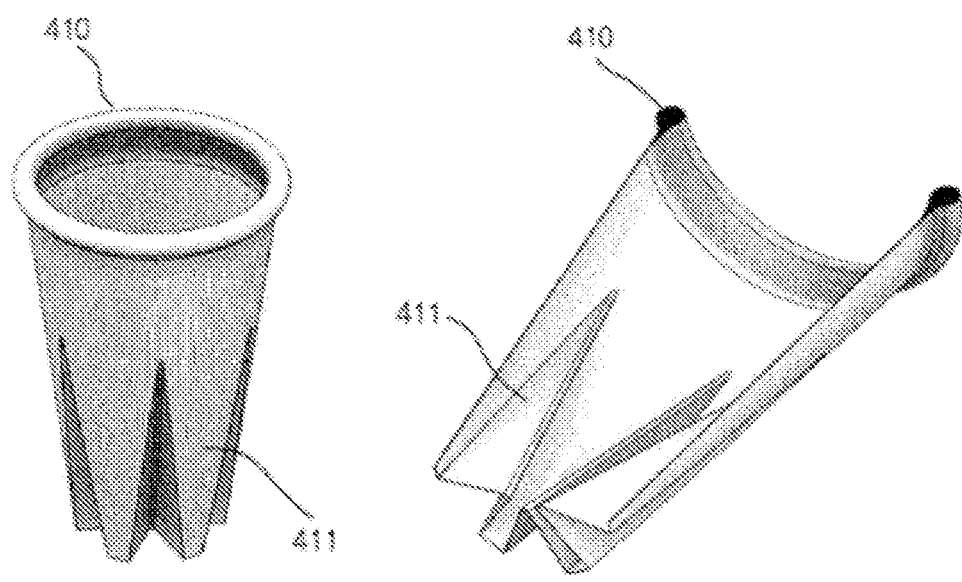

FIGS. 5 to 6 views of an anti-reflux valve for preventing gastro-esophageal reflux disease according to a fourth embodiment of the present invention.

Referring to FIGS. 5 to 6, an anti-reflux valve 40 for preventing gastro-esophageal reflux disease according to the fourth embodiment of the present invention may include a body 410 and a fixing clip 420. Hereinafter, a coupling structure between the body 410 and the fixing clip 420 may be the same as in FIGS. 2 to 4 described above, and thus, detailed descriptions of the coupling structure are omitted below, and only a structure of the body 410 will be described specifically.

The body 410 may include a reflux blocking portion 411 formed in a hopper shape having a diameter that is gradually reduced in a downward direction. The reflux blocking portion 411 may be formed of a thin and elastic material. When food goes down therethrough, a structure thereof may be expanded by elasticity to cause the food to go down. In addition, the reflux blocking portion 411 may be compressed by pressure, thereby preventing gastric contents from flowing backward.

In addition, the reflux blocking portion 411 may have an outer circumferential surface formed to have a wrinkle structure. In a case of the wrinkle structure, when food goes down therethrough, the wrinkle structure is more easily expanded by elasticity thereof and is also easily deformed by pressure, and thus, it is possible to more effectively prevent reflux of gastric contents due to compression by pressure.

In this case, the reflux blocking portion 411 may be formed of silicone, thermoplastic polyurethane (TPU), or so on, but the material is not limited thereto.

Figure 7:
FIG. 7 is a view illustrating a state in which a fixing clip of the present invention is coupled to a clip fastening tool.

Meanwhile, according to second to fourth embodiments of the present invention, when the fixing clip is fixed to the gastro-esophagus, a clip fastening tool illustrated in FIG. 7 may be used.

The anti-reflux valve for preventing gastro-esophageal reflux disease according to the present invention may be inserted into or mounted in an upper portion of the stomach of a patient with gastro-esophageal reflux disease to prevent endocrine fluid secreted from the stomach from refluxing through an upper end of the stomach, and thus, a potential effect of an anti-reflux surgery may be predicted.

Meanwhile, the embodiments of the present invention disclosed in the present specification and drawings are merely presented as specific examples to easily describe technical contents of the present invention and help understanding of the present invention and are not intended to limit the scope of the present invention. It will be apparent to those skilled in the art to which the present invention belongs that other modifications based on the technical idea of the present invention may be implemented in addition to the embodiments disclosed herein.

The invention claimed is:

1. An anti-reflux valve for preventing gastro-esophageal reflux disease, the anti-reflux valve configured to be installed in an upper portion of a stomach of a patient with gastro-esophageal reflux disease, the anti-reflux valve comprising:

a body formed in a ring shape and configured to be fixed to an upper end of a gastro-esophagus;

a reflux blocking plate coupled to an inner circumferential surface of the body to be rotatable in one direction; and a fixing clip coupled to the body and configured to fix the body to the upper end of the gastro-esophagus, wherein the reflux blocking plate comprises a first reflux blocking plate and a second reflux blocking plate that are vertically stacked on the body and coupled to sequentially rotate in a unidirectional manner to allow downward passage of food while preventing upward reflux, wherein the body comprises a first stepped portion supporting the first reflux blocking plate and a second stepped portion supporting the second reflux blocking plate, each of the first and second stepped portion being formed to limit a rotation of the respective reflux blocking plate.

2. The anti-reflux valve of claim 1, wherein the fixing clip is formed in a ring shape having one open region and coupled to the body such that the fixing clip is configured to be fixed to the gastro-esophagus.

3. The anti-reflux valve of claim 1, wherein the body has at least one coupling hole to which the fixing clip is fixed, and the fixing clip is coupled to the coupling hole such that the fixing clip is configured to be coupled to the gastro-esophagus.

4. The anti-reflux valve of claim 1, wherein the fixing clip is formed of a biodegradable material.

5. The anti-reflux valve of claim 1, wherein the body has a fixing groove formed therein to correspond to a shape of the fixing clip.

* * * * *